United States Patent [19]
Hunt

[11] Patent Number: 5,951,947
[45] Date of Patent: Sep. 14, 1999

[54] VACUUMIZED MICROWAVE DECONTAMINATION OF WASTE MATERIALS

[75] Inventor: James R. Hunt, Dunwoody, Ga.

[73] Assignee: A Creative Research and Testing Co, Dunwoody, Ga.

[21] Appl. No.: 09/041,965

[22] Filed: Mar. 13, 1998

[51] Int. Cl.[6] .............................. A61L 2/12; F26B 3/347; C05F 3/00
[52] U.S. Cl. .............................. 422/21; 34/263; 219/679; 219/695; 71/21
[58] Field of Search ................................ 422/21; 34/247, 34/259, 263; 219/635, 678, 679, 690, 695, 702; 71/21, 22, 64.01

[56] References Cited

U.S. PATENT DOCUMENTS

| | | |
|---|---|---|
| 3,997,388 | 12/1976 | Simon . |
| 4,193,786 | 3/1980 | Brill . |
| 4,622,446 | 11/1986 | Sugisawa et al. . |
| 5,003,143 | 3/1991 | Marks et al. ........................... 422/21 X |
| 5,270,000 | 12/1993 | Goldner et al. ........................... 422/21 |
| 5,276,924 | 1/1994 | Hachima . |

*Primary Examiner*—Elizabeth McKane
*Attorney, Agent, or Firm*—John Lezdey & Assoc

[57] ABSTRACT

A method for preparing fertilizer from animal, human and medical waste utilizing vacuumized microwave pathogen decontamination. The invention contemplates simultaneously heating the waste and reducing the pressure the reaction chamber in which the waste is located. As a result of the invention, the waste is decontaminated at a low temperature and the nutrients are preserved. The decontaminated waste is then mixed with a planting medium such as soil. The method may also include adding a diluting substance, chosen from the group consisting of humate, sawdust and sand, to dilute the nitrogen content of the disinfected waste.

7 Claims, 1 Drawing Sheet

VACUUMIZED MICROWAVE DECONTAMINATION OF WASTE MATERIALS

FIELD OF THE INVENTION

This invention relates to a method for preparing fertilizer from animal, human and medical waste using vacuumized microwave pathogen decontamination.

DESCRIPTION OF THE PRIOR ART

Some known methods of preparing fertilizer from animal, human and medical waste involve disinfecting by heating or incinerating the waste.

U.S. Pat. No. 5,287,818 to Rajamannan discloses a method of emitting microwave energy into the soil to kill soil organisms. According to Rajamannan, in carrying out the method, the soil is first pretreated by plowing to loosen soil compaction. Soil conditioners are then added to hasten break down of clods. Chemical or biological soil conditioners are effective in reducing clods to microaggregates. A biological soil conditioner which works extremely well is the commercial soil conditioner sold under the trademark SUPER SYMBEX by Agro-K Corporation Inc. of Minneapolis, Minn. A chemical soil conditioner is highly effective in reducing clods to microaggregates is ammonium laureth sulfate also sold by Agro-K Corporation Inc.

Microwave generator units are mounted on each of a plurality of subsurface tools that are components of a conventional agricultural implement. As the tools are moved through the soil, microwave energy is emitted and the energy elevates the temperature within the pathogenic organs to lethal levels.

U.S. Pat. No. 5,076,727 to Johnson et al. discloses a method of decontaminating soil by injecting moist, warm, clean air into a wells in the contaminated region. According to Johnson et al., moist warm air from a vapor treatment system is injected into wells which are screened (perforated) only at the contaminated depth forcing vapor flow only through the contaminated region. Intermediate the injection wells is an extraction well which is also screened only at the contaminated depth. A vacuum is drawn on the extraction well forcing the flushing vapors toward the extraction well through the contaminated soil, thereby entraining some of the contaminants. The contaminated, flushing vapor is then treated and recycled. An MW/RF heating system heats the earth's surfaces and the contaminated soil, thereby enhancing volatilization of the contaminants and their removal via the vapor flushing system. By screening the wells only through the contaminated zone and maintaining the contaminated soil zone in a moist state, the entire energy system is focused on the contaminated region.

While a method for microwaving in a vacuum is known, it has not been applied to the preparation of a fertilizer. U.S. Pat. No. 5,578,700 to Hunt et al., which is herein incorporated by reference, discloses a method of removing volatiles from rubber and recovering rubber crumb that utilizes microwave energy in a reduced pressure chamber.

Generally known methods utilizing microwaving waste destroys its nutrients. Microwaving according to prior art methods at temperatures sufficient to kill bacteria and viruses causes charring of the waste, which in turn destroys nutrients. In addition, microwaving at an effective temperature increases the temperature of the waste to such a degree that explosions often occur because of the presence of nitrates.

Preparing fertilizer from waste products heretofore has used either wastes infected with viruses and the like or wastes disinfected to such a degree that the nutrients have been destroyed. Therefore there exists a need for a simple and economical device and method for preparing fertilizer from animal, human and medical waste that will preserve the nutrients in the waste to a sufficient extent that the fertilizer will be both disinfected and capable of enhancing plant growth.

SUMMARY OF THE INVENTION

The preparation of fertilizer from waste heretofore traditionally has destroyed nutrients in the waste due to charring from the microwave heating. In addition, prior methods have caused explosions of the waste due to the presence of volatiles and/or nitrates during microwave heating at high temperatures. Alternatively, the fertilizer has contained bacteria and virus from the waste due to insufficient pathogen disinfecting.

This invention relates to a method for preparing fertilizer that optimizes the amount of soil nutrients in the waste. A feature of the invention consists of heating the waste by microwave energy to a low temperature while also reducing the pressure in the microwave chamber. The reduced pressure can be obtained by means of a vacuum pump. The combination of the microwave heating in the vacuum chamber results in increased disinfecting of the waste at a lower temperature. A result of the invention is the reduction of charring in the disinfected waste. In turn, the invention destroys fewer nutrients than the prior art methods. In addition, the likelihood of explosions is reduced in the current method.

The invention may also utilize a control board that receives information and controls settings for speed of movement of the waste through the chamber, temperature in the chamber, vacuumized pressure in the chamber and the like. In a preferred embodiment of the invention, there is provided two complete computer stations on each wave guide. One of the computers will take over operation if the other computer malfunctions.

The invention provides a method for preparing fertilizer from animal, human and medical waste which includes feeding waste into a reaction chamber having means to reduce pressure in the chamber and means to provide substantially precise microwave energy into the waste in the chamber, continuously moving the waste through the chamber, and reducing pressure in the chamber in conjunction with inputting energy into the waste in the chamber.

Optimally, there will be three to six microtrons with wave guides positioned on the reaction chamber irradiated at 1.0 to 5.0 GHZ using 3 kilowatts per guide unit.

Thereafter, the decontaminated waste material is withdrawn from the vacuum chamber. Its nitrogen content is diluted by adding diluting substances to the waste. Humate, sawdust, sand and the like are effective diluters.

The current invention provides the following benefits:

Provides plant nutrients both macro and micro;

Greatly increases root systems;

Improves growth of various groups of beneficial organisms;

Improves trace element nutrition through chelation;

Improves the quality of the color of harvested crops;

Affects the release of plant nutrients by organic decomposition;

Improves soil moisture conditions;

Holds exchangeable plant nutrients;

Aids in correcting plant chloroses;

Improves soil physical properties (fluffed non-crusted);

Increases plant efficiency by yielding more dry matter;

Increases capacity for water retention in soil by as much as 95%;

Functions as a respiratory catalyst;

Promotes soil drainage;

Participates actively in the decomposition of soil forming of rocks, minerals and organic material thereby creating new soil formation;

Produces stronger, faster growing seedlings;

Supplies biochemically active chelation compounds;

Prevents crusting of soils thereby increasing water acceptance;

Cell division is accelerated;

Prevents leaching of chemical fertilizers;

Decreases stress deterioration;

Increases protein and vitamin A content in forage and grains;

Speeds decomposition of poisons;

Improves ability of resist frost and pests due to hardiness;

Produces stronger and healthier plants;

Speeds reduction of field stubble into needed humus;

Intensifies the enzyme systems;

Assists in balancing of the soil pH;

Increases of 100% or more in plant yields are not uncommon;

Increases the permeability of plant membranes;

Reduces the need for chemical fertilization by as much as 95%;

Increases the germination capacity of seed;

Reduces soil erosion;

Serves as an organic catalyst for all plant functions;

Increases shelf storage life of produce up to 8 additional days;

Supplies the need humus at a fraction of the cost;

Improves soil structure formation via aeration;

Improves the sugar content of fruits and vegetables up to 9%;

Spurs plant growth via presence of auxin type reactions;

Increases plant recovery ability after damage, pruning or mowing;

Increases nutrient availability via enhanced exchange and buffering properties.

The principle object of this invention is the provision of a method for preparing fertilizer from animal, human and medical waste that will have an increased nutrient content.

A further object of the invention is a method for preparing from animal, human and medical waste a fertilizer that contains natural growth stimulants. The natural growth stimulants that can be an end product of the current invention are similar to humate.

A still further object of the invention is a method for preparing from animal, human and medical waste a fertilizer that contains chelating agents. A chelating agent that can be produced by the current invention is mannitol.

Another object of the invention is to speed up decomposition and purification productivity of the waste.

Yet another object of the invention is to create waste that is decontaminated from pathogens and that also has a high nitrogen content.

Other objects and advantages of this invention will become apparent from the following description taken in connection with the accompanying drawing wherein is set forth by way of illustration and example an embodiment of this invention.

BRIEF DESCRIPTION OF THE PREFERRED EMBODIMENTS

Figure 1:
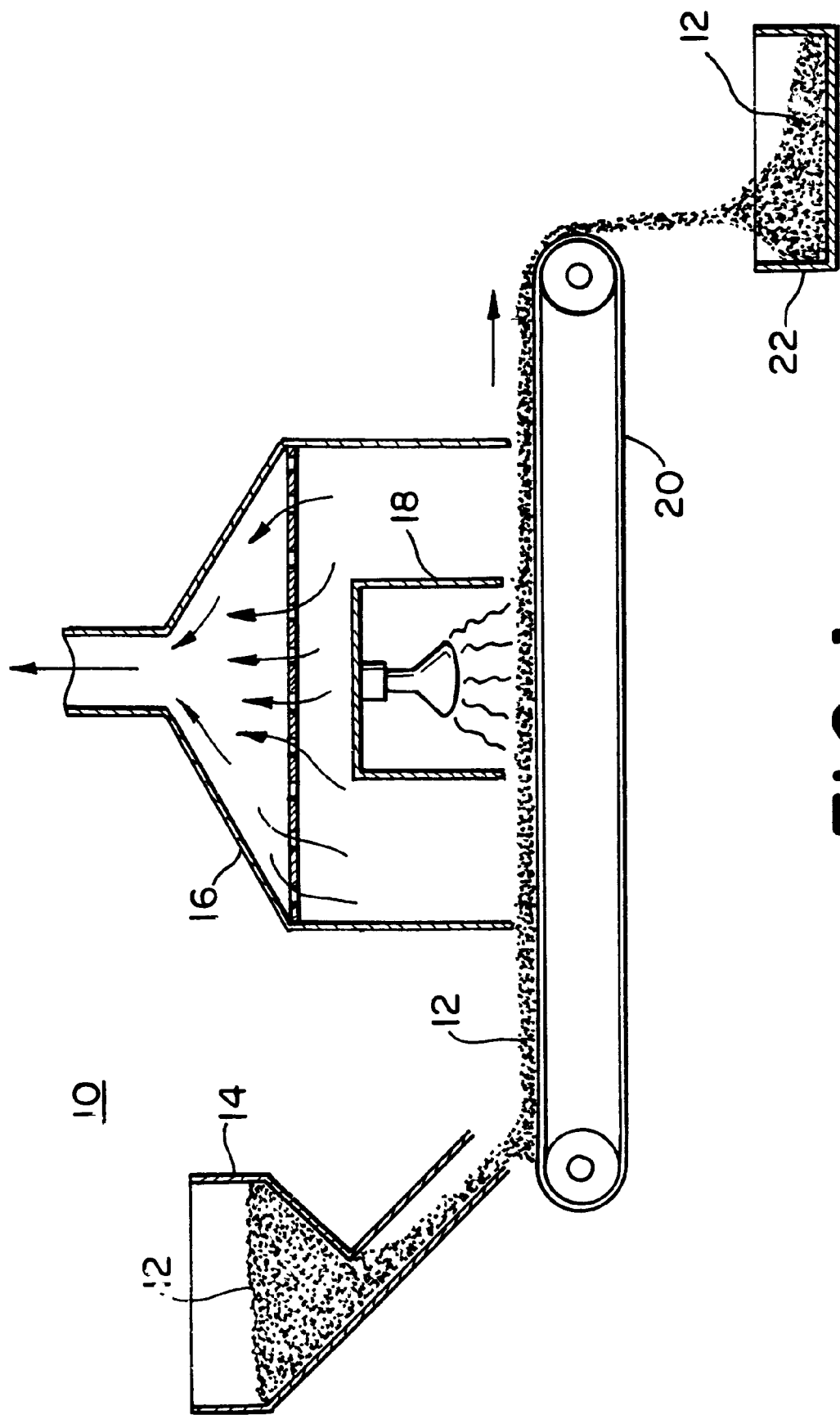
FIG. 1 is an elevational cross-sectional view of an apparatus utilizing the method of the present invention in a preferred embodiment.

Referring to FIG. 1, there is illustrated an apparatus 10 for performing the methods of the invention. The waste 12, which may be animal, human or medical waste, is fed into a receptacle 14 that funnels the waste 12 to a vacuumized reaction chamber 16. The reaction chamber 16 has both a means to reduce the pressure in the chamber and a means to provide substantially precise energy into the waste. While in the reaction chamber 16, the waste 12 is conveyed to the irradiation chamber 18 where it is simultaneously subjected to the reduced pressure of the reaction chamber 16 and the microwave energy of the irradiation chamber 18 wherein the waste is disinfected. A conveyance means 20 is provided whereby the disinfected waste 12 is transported by a conveyor belt 20 from the reaction chamber 16 to a collection receptacle 22. Thereafter, the disinfected waste 12 is combined with a planting medium (not shown).

While a wide variety of planting mediums may be used, the most common is soil. In another preferred embodiment of the invention, the disinfected waste 12 may be diluted with a diluting substance (not shown) chosen from a group consisting essentially of humate, sawdust, and sand.

Preferably, the reduced pressure in the reaction chamber 16 is by means of a vacuum, which may be created from a vacuum pump.

The energy source in the irradiation chamber 18 preferably is from microwaves.

Accordingly there is provided a method for preparing fertilizer from animal, human and medical waste 12 comprising the steps of feeding waste 12 into a reaction chamber 16 having means to reduce pressure in the chamber 16 and means to provide substantially precise energy into the waste 12 in the chamber 16. The waste 12 is continuously moved through the chamber 16 where it is subjected to reduced pressure and energy input whereby the waste 12 is disinfected. The disinfected waste 12 is discharged from the chamber 16 and combined with a planting medium.

While any planting medium may be used, the most common is soil. In addition, according to the invention, the disinfected waste 12 may be diluted with a diluting substance chosen from a group consisting essentially of humate, sawdust and sand. The diluting substance dilutes the amount of nitrogen and other substances and nutrients remaining in the disinfected waste 12 to create an optimal mixture for fertilizing.

Although any kind of animal, human or medical waste 12 can be disinfected by the invention, disinfecting Suidae manure, preferably pig manure is particularly advantageous because before it is disinfected it is known to contain bacteria, viruses and other pathogens.

The reduction of pressure may be accomplished by many means. However, creating a vacuum by a vacuum pump is preferred.

Similarly, while the added energy may be provided by many means, microwaves are preferred. Optimally, the microwaves are created using three to six microtrons having wave guides and being positioned on the chamber irradiated at 1.0 to 5.0 GHZ. The irradiation is accomplished by means of three to five microwave guides, with each guide using three kilowatts per unit.

The combination of the reduction of the subatmospheric pressure in the chamber 16 with the input of energy, preferably from microwaves, enables the waste 12 to be disinfected at a lower temperature than that known in the prior art. Accordingly, when practicing the present invention, the temperature needed to disinfect the waste 12 is within the range of about 65° to 95° Fahrenheit, whereas at atmospheric pressure, the temperature needed is in the range of 212° to 214° Fahrenheit.

Pursuant to the invention, the preferable temperature needed to disinfect different kinds of waste varies with the elements composing the waste. The preferable temperature is between 70° to 75° Fahrenheit for pig manure. For medical waste, the preferable temperature is slightly higher at 75° to 95° Fahrenheit. Conversely, for cow manure, the preferable temperature is slightly lower at 65° to 70° Fahrenheit.

The invention also may utilize two complete computer stations on each microwave guide. Each computer serves as a backup to the other.

What is claimed is:

1. A method for preparing fertilizer from animal waste containing soil nutrients and pathogens consisting essentially of the steps of:

feeding waste into a vacuum chamber having means to reduce pressure throughout said chamber and means to provide substantially precise microwave energy into said waste in said chamber;

continuously moving said waste through said chamber;

reducing pressure in said chamber in conjunction with inputting said microwave energy of about 1.0 to 5.0 GHZ into said waste in said chamber so as to remove volatiles without charring the waste to control a temperature of about 65° to 95° F. in said chamber, wherein the waste is disinfected and the amount of soil nutrients is optimized;

discharging disinfected waste from said chamber; and combining disinfected waste with a planting medium.

2. The method of claim 1 wherein the planting medium is soil.

3. The method of claim 1 wherein the said disinfected waste is diluted with a diluting substance chosen from a group consisting essentially of humate, sawdust and sand.

4. The method of claim 1 wherein the said waste is manure from mammals of the family Suidae.

5. The method of claim 1 wherein the microwaves are created using three to six microtrons having wave guides, said microtrons being positioned on said chamber irradiated at 1.0 to 5.0 GHZ.

6. The method of claim 1 wherein the said irradiation is accomplished by means of three to five microwave guides; each said guide using three kilowatts per unit.

7. The method of claim 1 utilizing two complete computer stations on each microwave guide; each said computer serving as a backup to the other.

* * * * *